United States Patent [19]

Papenfuhs

[11] 4,081,446

[45] Mar. 28, 1978

[54] PROCESS FOR THE PREPARATION OF 4-AMINO-1,8-NAPHTHALIC ACID-N-ARYLIMIDES

[75] Inventor: Theodor Papenfuhs, Frankfurt am Main, Germany

[73] Assignee: Hoechst Aktiengesellschaft, Frankfurt am Main, Germany

[21] Appl. No.: 728,923

[22] Filed: Oct. 4, 1976

Related U.S. Application Data

[63] Continuation of Ser. No. 572,753, Apr. 29, 1975, abandoned.

[30] Foreign Application Priority Data

May 15, 1974 Germany .............................. 2423546

[51] Int. Cl.² ......................................... C07D 221/14
[52] U.S. Cl. ......................... 260/281 N; 260/281 NH; 260/281 S
[58] Field of Search ......... 260/281 N, 281 NH, 281 S

[56] References Cited

FOREIGN PATENT DOCUMENTS

| 469,018 | 10/1950 | Canada | 260/281 N |
| 469,152 | 11/1950 | Canada | 260/281 N |
| 47/08466 | 10/1968 | Japan | 260/281 N |

OTHER PUBLICATIONS

Bullock et al., J. Amer. Chem. Soc. 78, 3693 (1956).
Boyer et al., Organic Syn. 40, pp. 96–99, (1960).

*Primary Examiner*—R. Gallagher
*Assistant Examiner*—Mark L. Berch
*Attorney, Agent, or Firm*—Connolly and Hutz

[57] ABSTRACT

4-Amino-1,8-naphthalic acid-N-arylamides are obtained by reacting 4-halo-1,8-naphthalic acid-N-arylamides with ammonia in an anhydrous polar organic solvent. The products are colorants for solvents or daylight-fluorescence pigments.

5 Claims, No Drawings

PROCESS FOR THE PREPARATION OF 4-AMINO-1,8-NAPHTHALIC ACID-N-ARYLIMIDES

This application is a continuation of application Ser. No. 572,753 filed Apr. 29, 1975 now abandoned.

The present invention relates to an improved process for the preparation of 4-amino-1,8-naphthalic acid-N-arylimides.

4-Amino-1,8-naphthalic acid-N-arylimides, in particular the 2', 4'-xylidide, have become important pigments, dispersion and solvent dyestuffs (cf. C.I. 56 200 in Colour Index, 3rd edition (1971), vol. 4, page 4508).

The said compounds can be prepared by way of nitrating acenaphthene, by oxydizing the 5-nitro-acenaphthene so obtained with potassium bichromate to give the 4-nitro-1,8-naphthalic acid anhydride, by reducing the latter compound to give the 4-amino-1,8-naphthalic acid-anhydride, and finally by reacting the product obtained with an aromatic amine, or by reacting the 4-nitro-1,8-naphthalic acid anhydride with an aromatic amine to give the ammonium salt of the 4-nitro-naphthalic acid, by reducing the product obtained and converting it into the 4-amino-1,8-naphthalic acid-N-arylimide by splitting off the amine at elevated temperatures (cf. German Auslegeschrift No. 1,046,622 and U.S. Pat. Nos. 1,796,012, 2,474,185 and 2,715,126). These processes have the drawback that they are very complicated, and that their implementation on an industrial scale is very expensive, due to the use of the high-cost oxydation agent of potassium bichromate and the additional use of organic solvents to be regenerated in the process of nitration, and also owing to the very poor yields which are partially obtained.

It has now been found that 4-amino-1,8-naphthalic acid-N-arylimides of the formula I

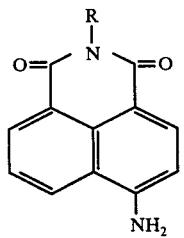

(I), in which R represents an aromatic radical, can be prepared in a way which is considerably simpler and less expensive, which comprises reacting a 4-halogeno- 1,8-naphthalic acid-N-arylimide of the formula II

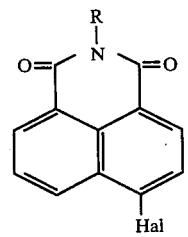

(II), wherein Hal is a halogen atom and R has the above-mentioned meaning, with ammonia in an anhydrous polar organic solvent.

The process of the invention is effected in such a way that the 4-halogeno-1,8-naphthalic acid-N-arylimide, in particular a 4-chloro- or 4-bromo-1,8-naphthalic acid-N-arylimide, is suspended in a polar organic solvent, preferably an aliphatic alcohol having from 1 to 6 carbon atoms, a lower alkane-carboxylic acid-amide, such as dimethyl-formamide, a cyclic ether, such as tetrahydrofuran or dioxan, or a glycolether, is then heated at a temperature in the range of from about 150° to 200° C, preferably from about 160° to 180° C, for several hours, after excess anhydrous ammonia and, optionally, catalytic amounts of copper powder or copper compounds have been added, and the 4-amino-naphthalic acid-N-arylimide formed is isolated by filtration and dried after cooling and releasing the pressure.

The filtrate can be regenerated by distillation and can be used for a further reaction, after the ammonia has been made up.

Of the solvents used, preference is given to alkanols having from 3 to 5 carbon atoms, in particular isopropanol and isobutanol, as well as glycolethers, such as glycolmono- and -dimethylether, especially ethyleneglycolmono- and -dimethylether. The process of the invention yields optimal results, above all, with isopropanol.

The 4-halogeno-1,8-naphthalic acid-N-arylimides used as starting products are easily accessible, for example, by condensing 4-halogeno-1,8-naphthalic acid anhydride with stoichiometrical amounts of an arylamine in an acid, optionally aqueous, medium at an elevated temperature, optionally under pressure. Starting products of this kind are known, for example, from Chemical Abstracts, vol. 48, 11791 e, vol. 54, 24580 a and vol. 61, 624 a. They can be obtained in an excellent yield and purity. Their preparation has been described in the abovementioned literature.

It was a surprising fact which could not have been foreseen that the process of the invention results in products of an excellent purity which as a rule do not require a purification by way of recrystallization. Hitherto, every attempt to obtain 4-amino-1,8-naphthalic acid-N-arylimides, which can be used on an industrial scale, from 4-halogeno-1,8-naphthalic acid-N-arylimides, by using aqueous or liquid ammonia, optionally in the presence of unpolar solvents, has been unsuccessful due to the simultaneous formation of 4-amino-naphthalimide according to the equation

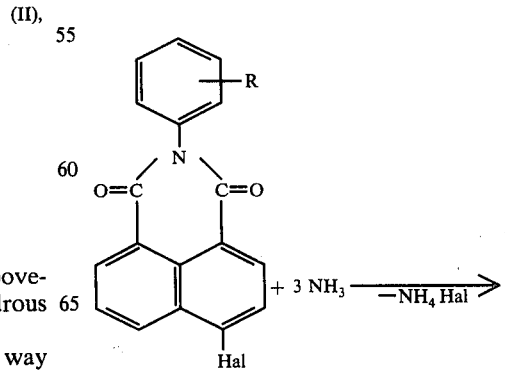

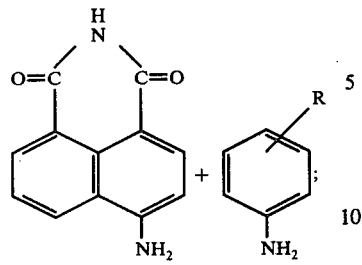

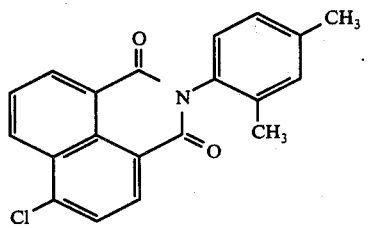

however, these by-products cannot be separated from the desired dyestuff but with high expenditure, so that the known processes lead to products, the quality of which is totally unsatisfactory.

In contradistinction thereto, the process of the invention yields the dyestuffs as almost analytically pure products which are completely free from 4-amino-1,8-naphthalimide and which can be used, in this form, directly for the dyeing of solvents and polyester materials, such as polyester fibers, but particularly for the preparation of daylight-fluorescence pigments.

The process of the invention is suitable in particular for the preparation of 4-amino-1,8-naphthalic acid-N-phenyl- or -N-naphthalimide or of 4-amino-1,8-naphthalic acid-N-phenyl or -N-naphthylimides containing non-ionogenic substituents in the phenyl or naphthyl moieties, such as halogen atoms, particularly chlorine or bromine atoms, alkyl- or alkoxy groups having from 1 to 6 carbon atoms, in particular methyl, ethyl, isopropyl, butyl, methoxy and ethoxy groups, cyano, acyl groups of lower alkane-carboxylic acids or of aromatic carboxylic acids, for example, acetyl, propionyl or benzoyl groups, hydroxy, lower alkylsulfonyl, arylsulfonyl groups, such as the phenylsulfonyl, trifluoromethyl, carbalkoxy groups, in particular carbomethoxy and carboethoxy groups, acylamino groups of lower alkane carboxylic acids or of aromatic carboxylic acids of aromatic sulfonic acids, such as acetylamino, benzoylamino or oxalylamino groups, ureido, carbonamide, sulfonamide or optionally substituted amino groups, such as dimethylamino or diethylamino groups.

Preference is given particularly to such products of the process of the invention as, for example, 4-amino-1,8-naphthalic acid-N-phenylimides which are substituted in the phenyl moiety by from 1 to 3 methyl groups or by 1 to 2 halogen atoms, in particular the 4-amino-naphthalic acid-2′, 4′-xylidide.

The following Examples serve to illustrate the process of the invention. The parts are parts by weight.

EXAMPLE 1 a. A mixture of 349 parts of 4-chloronaphthalic acid anhydride, 190 parts of asymmetrical m-xylidine and 1600 parts of glacial acetic acid was boiled for 8 hours under reflux (115° C). After cooling, the product was suction-filtered, was washed until neutral and was dried. 480 Parts of 4-chloro-naphthalic acid-m-xylidide were obtained which corresponded to the formula b. 67 Parts of this compound were suspended, together with 0.1 part of copper powder, in 800 parts of isopropanol, and the suspension was placed into an autoclave. Subsequently from 40 to 50 parts of anhydrous ammonia gas were introduced under pressure into the closed autoclave, and the reaction mixture was stirred for 20 hours at 170° C. A pressure of from 20 to 25 atmospheres gage was established.

After cooling and releasing the pressure, the product was suction-filtered, was washed with isopropanol and dried. 60 Parts of 4-amino-naphthalic acid-m-xylidide were obtained which had the formula

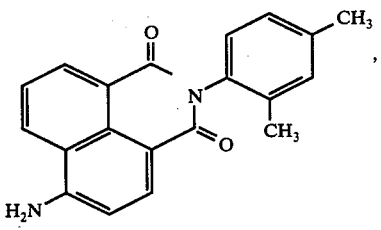

which corresponded to a yield of 95% of the theory. The absorption maximum (measured in dimethylformamide) was at 429 nm, the fluorescence maximum (measured in dimethylformamide) was at 517 nm.

A relative fluorescence intensity of 102% was found, as compared against a chemically identical commercial product.

If instead of isopropanol the same amounts of ethyleneglycol-monomethylether were used, the same dyestuff was obtained in the same quality, however, in a slightly reduced yield.

EXAMPLE 2 a. 277 Parts of 4-bromonaphthalic acid anhydride were heated for 12 hours at a temperature in the range of from 120° to 130° C in the autoclave, together with 10 parts of acetic acid, 140 parts of 4-chloroaniline and 1550 parts of water; after cooling, the product was suction-filtered, was washed until neutral and dried. 380 Parts of 4-bromonaphthalic acid-p-chloroanilide were obtained which had the formula

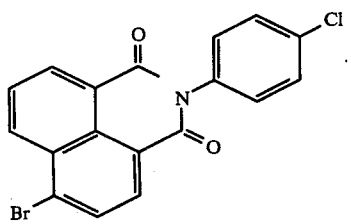

b. 38.65 Parts of this compound, 0.1 part of copper-(I)-chloride and 400 parts of isobutanol were introduced into an autoclave, were mixed with from 20 to 25 parts of liquid ammonia and were then heated for 16 hours at 180° C at a pressure of from 25 to 28 atmospheres gage. Then the reaction mixture was cooled to 20° C, the pressure was released, the reaction product was suction-filtered, was washed with isobutanol and dried. 31 Parts (96% of the theory) of 4-amino-naphthalic acid-p-chloroanilide were obtained which had the formula

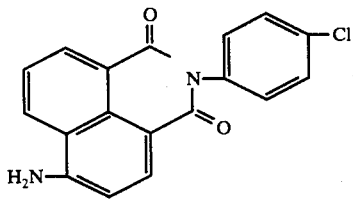

As compared against the one mentioned in Example 1, this dyestuff showed a fluorescence intensity which was slightly lower. Its absorption maximum (measured in dimethylformamide) was at 426 nm, the fluorescence maximum (measured in dimethylformamide) was at 516 nm. This dyestuff was extremely suitable for the preparation of luminescent pigments on the basis of a melamine/formaldehyde/toluenesulfonamide resin, which are fluorescent at daylight, and it is marked by its particularly greenish color shade.

If instead of isobutanol the same amounts of tetrahydrofuran were used, the same dyestuff was obtained in a yield that was even better, however, the quality was slightly reduced.

EXAMPLES 3 to 19

According to the process variants of Example 1 or 2, further dyestuff precursors of the formula II

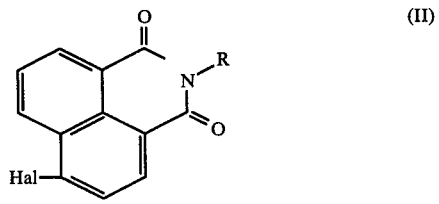

can be reacted with ammonia according to the invention.

These products were prepared according to a method analogous to Examples 1a and 2a. The compounds of formula I thus obtained were partially new, for the other part they had already been prepared in a complicated operation according to the method described above.

| | Preparation of the starting product | | | Reaction with ammonia | | $\lambda_{max}$[nm] in DMF | |
|---|---|---|---|---|---|---|---|
| Ex. | Hal | R | Yield % | Solvent | Yield % | of absorpt. | of fluoresc. |
| 3 | Cl | (phenyl) | 89.5 | isopropanol | 84.7 | 430 | 519 |
| 4 | Cl | (3-chlorophenyl) | 93.0 | ethylene-glycol-methylether | 92.8 | 426 | 517 |
| 5 | Cl | (4-methylphenyl) | 96.0 | isobutanol | 89.0 | 429 | 518 |
| 6 | Br | (benzimidazolone) | 99.2 | isobutanol | 97.5 | 423 | 515 |
| 7 | Cl | (2,4,6-trimethylphenyl) | 92.8 | isopropanol | 92.6 | 429 | 517 |
| 8 | Cl | (2,4-dichlorophenyl) | 97.5 | isopropanol | 95.5 | 424 | 515 |
| 9 | Br | (4-cyanophenyl) | 87.6 | isopropanol | 92.8 | 423 | 515 |
| 10 | Br | (4-bromophenyl) | 96.8 | isobutanol | 94.0 | 426 | 515 |

-continued

| Ex. | Hal | R | Yield % | Solvent | Yield % | λ_max[nm] in DMF of absorpt. | of fluoresc. |
|---|---|---|---|---|---|---|---|
| 11 | Cl | (phenyl with Br) | 95.2 | ethylene-glycol-monomethyl-ether | 92.8 | 426 | 515 |
| 12 | Cl | (phenyl with NHCOCH₃) | 98.9 | ethylene-glycol-monomethyl-ether | 90.3 | 423 | 514 |
| 13 | Cl | (phenyl with COCH₃) | 92.1 | ethylene-glycol-monomethyl-ether | 88.0 | 428 | 517 |
| 14 | Cl | (naphthyl) | 90.5 | isobutanol | 88.5 | 427 | 518 |
| 15 | Cl | (naphthyl with CH₃) | 92.4 | isopropanol | 90.1 | 427 | 517 |
| 16 | Br | (phenyl with OCH₃, OCH₃) | 86.7 | isopropanol | 94.8 | 436 | 523 |
| 17 | Br | (phenyl with OH) | 85.8 | isopropanol | 86.2 | 433 | 521 |
| 18 | Br | (phenyl with SO₂CH₃) | 97.4 | ethylene-glycol-methylether | 95.1 | 428 | 517 |
| 19 | Cl | (phenyl with NH₂) | 89.0 | | 83.9 | 435 | 522 |

EXAMPLE 20

35 Parts of 4-chloronaphthalic acid-mesidide (cf. Ex. 7) and 0.1 part of copper bronze were suspended in 250 parts of N-methylpyrrolidone saturated with ammonia gas at room temperature; the mixture was heated in an autoclave at 165° C for 12 to 14 hours, in which process a pressure of from about 12 to 16 atmospheres gage was established. Then the reaction mixture was cooled, the pressure was released, 300 parts of ethanol added and the product was suction-filtered, washed with ethanol and dried. 29 Parts of 4-amino-naphthalic acid-mesidide were obtained which had the formula

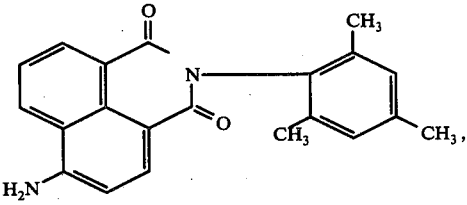

which corresponded to a yield of 88% of the theory. The dyestuff had the absorption and fluorescence spectrum (measured in dimethyl-formamide) mentioned in Example 7 which corresponded to that of the product mentioned in Example 1 and was therefore extremely suitable for the preparation of yellow daylight-fluorescence pigments on the basis of a melamineformaldehyde/toluene-sulfonamide resin which showed in some cases a fastness to light that was slightly superior to that of the fluorescence pigments prepared with the dyestuff of Example 1.

If instead of N-methylpyrrolidone use was made of dimethylformamide as solvent in the reaction, the product was obtained in a comparable yield and quality.

In the following Examples, advantageous processes for the preparation of the starting materials have been described. Analogous compounds are accessible according to the same processes.

a. 116.0 Parts of 4-chloronaphthalic acid anhydride and 98.5 parts of as.-m-xylidine were introduced successively into 500 parts of N-methylpyrrolidone, and the mixture was heated to a temperature of from 130° to 135° C, until a chromatographic examination indicated the complete absence of the starting product (about 8 hours). Subsequently the reaction mixture was cooled to 70° C, was diluted with 650 parts of methanol and was cooled further to room temperature. After suction-filtration, washing with methanol and water and drying at 80° C, 157 parts of 4-chloronaphthalic acid-m-xylidide were obtained which had the formula

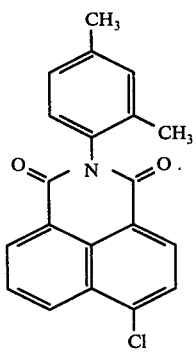

Other methods of preparing the chloronaphthalimides are as follows:

b. 465 Parts of 4-chloronaphthalic acid anhydride and 254 parts of asymmetrical m-xylidine were dissolved in 2200 parts of glacial acetic acid, the mixture was heated for 8 hours at a temperature of from 110° to 120° C, subsequently the product was cooled, was suction-filtered, washed with water until neutral and dried at 80° C. 518 Parts (77% of the theory) of 4-chloronaphthalic acid-m-xylidide were obtained which had the above formula.

c. 232.5 Parts of 4-chloronaphthalic acid anhydride, 125 parts of as.-m-xylidine, 5 parts of acetic acid and 1000 parts of water were heated in an autoclave having a stirring device for 10 hours at a temperature in the range of from 130° to 140° C. Thereafter the reaction mixture was freed from the excess xylidine by distillation with steam after having released the pressure. Then the product was suction-filtered, was washed and dried. 322 Parts of 4-chloronaphthalic acid-m-xylidide were obtained which had the above formula.

d. 277 Parts of 4-bromonaphthalic acid anhydride, 89 parts of 3-amino,1,2,4-triazole and 1000 parts of dimethylformamide were heated for 6 hours at 130° C. After 650 parts of methanol had been added and the mixture had been cooled to room temperature, the product was suctionfiltered, was washed with methanol and water and was dried at 80° C. 330 Parts of 4-bromonaphthalic acid-(1', 2', 4'-triazolyl-3')-imide were obtained which had the formula

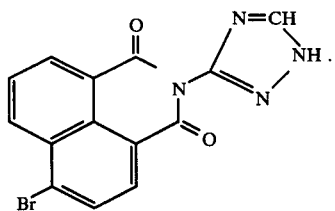

If instead of dimethylformamide, use was made of the same amounts of dimethylsulfoxide, N-methylacetamide or phosphoric acid-tris-dimethylamide, the compound was obtained in the same yield.

I claim:
1. A process for the preparation of a compound of the formula

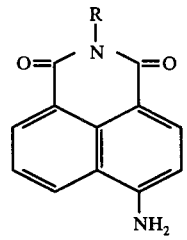

wherein R is phenyl or naphthyl which are unsubstituted or substituted by 1 to 3 substituents selected from alkyl or alkoxy of 1 to 6 carbon atoms each, cyano, alkanoyl of 1 to 4 carbon atoms, benzoyl, benzenesulfonyl, toluenesulfonyl, alkylsulfonyl of 1 to 4 carbon atoms, hydroxy, trifluoromethyl, carboalkoxy of 1 to 4 carbon atoms in the alkyl moiety, alkanoylamino of 1 to 4 carbon atoms, benzoylamino, alkylsulfonylamino of 1 to 4 carbon atoms, benzenesulfonylamino, toluene-sulfonylamino, ureido, carbamoyl, sulfamoyl, amino, mono- or dialkylamino with alkyl moieties of 1 to 4 carbon atoms each, chlorine or bromine which comprises reacting a compound of the formula

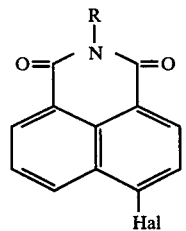

wherein R is as defined above and Hal is halogen, with ammonia under pressure in an anhydrous polar organic solvent at a temperature of from 150° to 200° C, said solvent being an alkanol of 1 to 6 carbon atoms, dimethylformamide, tetrahydrofuran, dioxan or a mono- or diether or ethylene glycol with alkanols of 1 to 4 carbon atoms.

2. A process as claimed in claim 1, wherein the temperature is from 160° to 180° C.

3. A process as claimed in claim 1, wherein Hal is chlorine or bromine.

4. A process as claimed in claim 1, wherein the solvent is an alkanol of 3 to 5 carbon atoms.

5. A process as claimed in claim 1, wherein R is phenyl which is unsubstituted or substituted by 1 to 3 methyl or 1 or 2 chlorine or bromine atoms.

* * * * *